US010448589B2

(12) United States Patent
Silvertand

(10) Patent No.: US 10,448,589 B2
(45) Date of Patent: Oct. 22, 2019

(54) TOMATO VARIETY NUN 09168 TOF

(71) Applicant: Nunhems B.V., Nunhems (NL)

(72) Inventor: Bernard Catharina Hubert Silvertand, AB Nunhem (NL)

(73) Assignee: NUNHEMS B.V., Nunhem (NL)

( * ) Notice: Subject to any disclaimer, the term of this patent is extended or adjusted under 35 U.S.C. 154(b) by 43 days.

(21) Appl. No.: 15/384,526

(22) Filed: Dec. 20, 2016

(65) Prior Publication Data

US 2017/0099796 A1    Apr. 13, 2017

(30) Foreign Application Priority Data

Dec. 23, 2015    (EP) ..................................... 15202573

(51) Int. Cl.
*A01H 5/08* (2018.01)
*A01H 5/10* (2018.01)

(52) U.S. Cl.
CPC ..................................... *A01H 5/08* (2013.01)

(58) Field of Classification Search
None
See application file for complete search history.

(56) References Cited

U.S. PATENT DOCUMENTS

2015/0074839 A1* 3/2015 Engels ..................... A01H 5/08
                                                     800/260

FOREIGN PATENT DOCUMENTS

| EP | 1428425 A1 | 6/2004 |
| WO | 1998024301 A1 | 6/1998 |
| WO | 1999021411 A1 | 5/1999 |
| WO | 200074468 A1 | 12/2000 |
| WO | 2008143504 A1 | 11/2008 |
| WO | 2008143504 A2 | 11/2008 |
| WO | 2013182646 A1 | 12/2013 |
| WO | 2014076249 A1 | 5/2014 |

OTHER PUBLICATIONS

Wijnker et al, 2014, Nature Protocols, 9:761-772.*
Acquaah, "Principles of Plant Genetics and Breeding", 2007, Blackwell Publishing, ISBN-13: 978-1-4051-3646-4.
Wijnker et al., "Hybrid recreation by reverse breeding in *Arabidopsis thaliana*", Nature Protocols, 2014, vol. 9, No. 4, pp. 761-772. DOI: 10.1038/nprot.2014.049.
Vidavsky and Czosnek, "Tomato Breeding Lines Resistant and Tolerant to Tomato Yellow Leaf Curl Virus Issued from Lycopersicum hirsutum", Phytopathology, 1998, vol. 88, No. 9, pp. 910-914.
Ince et al., "Genetic Relationships Within and Between *Capsicum* Species", Biochem. Genet., 2010, vol. 48, pp. 83-95.
Vos et al., "AFLP: a new technique for DNA fingerprinting", Nucleic Acids Research, 1995, vol. 23, No. 21, pp. 4407-4414.
Dorais and Papadopoulos, "Greenhouse Tomato Fruit Quality", Horticultural Reviews, 2001, vol. 26, pp. 239-319.
Bhatia et al., "Tissue culture studies of tomato (*Lycopersicon esculentum*", Plant Cell, Tissue and Organ Culture, 2004, vol. 78, pp. 1-21.
UPOV (International Union for the Protection of New Varieties and Plants), "Guidelines for the Conduct of Tests for Distinctness, Uniformity and Stability, TG/44/10" (Geneva 2001) upov.int/en/publications/tg-rom/tg044/tg_44_10.pdf.
US Department of Agriculture, Agricultural Marketing Service, Plant Variety Protection Office, Beltsville, MD 20705 "Objective Description of Variety Tomato (*Lycopersicon esculentum* Mill.)", http://www.ams.usda.gov/sites/default/files/media/55-Tomato%20ST-470-55%202015.pdf.

* cited by examiner

*Primary Examiner* — Jason Deveau Rosen

(74) *Attorney, Agent, or Firm* — Arent Fox LLP

(57) ABSTRACT

The invention provides a new and distinct hybrid variety of tomato, NUN 09168 TOF.

18 Claims, No Drawings

TOMATO VARIETY NUN 09168 TOF

FIELD OF THE INVENTION

The present invention relates to the field of plant breeding and, more specifically, to the development of tomato variety NUN 09168 TOF (also designated as NUN 09168 or NUN 9168 or NUN 09168 F1 or NUN 09168 hybrid). The invention further relates to vegetative reproductions of NUN 09168 TOF, methods for in vitro tissue culture of NUN 09168 TOF, explants and also to phenotypic variants of NUN 09168 TOF.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different varieties produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential. One crop species which has been subject to such breeding programs and is of particular value is the tomato.

Tomato (*Solanum lycopersicum* and closely related species) is naturally a diploid and the basic chromosome number of the genus is x=12, most are 2n=2x=24, including the cultivated ones. It originated in the New World and has since become a mayor food crop. In 2012, FAOSTAT estimated world production at over 160 million tonnes.

Tomato cultivars may be grouped by maturity, i.e. the time required from planting the seed to the stage where fruit harvest can occur. Standard maturity classifications include 'early', 'midseason' or late-maturing'. Another classification for tomatoes is the developmental timing of fruit set. 'Determinate' plants grow foliage, then transition into a reproductive phase of flower setting, pollination and fruit development. Consequently, determinant cultivars have a large proportion of the fruit ripen within a short time frame. Growers that harvest only once in a season favor determinant type cultivars. In contrast, 'indeterminate' types grow foliage, then enter a long phase where flower and fruit development proceed along with new foliar growth. Growers that harvest the same plants multiple times favor indeterminate type cultivars. In response to more recent consumer demands for dietary diversity, tomato breeders have developed a wider range of colors. In addition to expanding the range of red colored fruits, there are cultivars that produce fruits that are creamy white, lime green, yellow, green, golden, orange and purple. Additionally, there are multi-colored varieties exemplified by mainly red fruited varieties with green shoulders, and both striped- and variegated-colored fruit.

The fruits of tomato plants which are more suitable for processing are generally red colored and have pink to red/crimson fruit flesh.

SUMMARY OF THE INVENTION

In one aspect of the invention, a seed of tomato variety NUN 09168 TOF is provided, wherein a representative sample of said seed has been deposited under Accession Number NCIMB 42501. The tomato seed of the invention may be provided as an essentially homogeneous population of tomato seed. Therefore, seed of the invention may be defined as forming at least about 97% of the total seed, including at least about 98%, 99% or more of the seed. The population of tomato seed may be particularly defined as being essentially free from other seed. The seed population may be separately grown to provide an essentially homogeneous population of tomato plants according to the invention. Also encompassed are plants grown from seeds of tomato variety NUN 09168 TOF and plant parts thereof.

In another aspect the invention provides for a hybrid variety of *S. lycopersicum* called NUN 09168 TOF. The invention also provides for a plurality of seeds of the new variety, plants produced from growing the seeds of the new variety NUN 09168 TOF, and progeny of any of these. Especially, progeny retaining one or more (or all) of the "distinguishing characteristics" or one or more (or all) of the "essential morphological and physiological characteristics" or essentially all physiological and morphological characteristics of NUN 09168 TOF referred to herein, are encompassed herein as well as methods for producing these.

In one aspect, such progeny have all the physiological and morphological characteristics of tomato variety NUN 09168 TOF when grown under the same environmental conditions. In another aspect such progeny have all the physiological and morphological characteristics as listed in Table 1 and/ or 2 as tomato variety NUN 09168 TOF when measured under the same environmental conditions (i.e. evaluated at significance levels of 1%, 5% or 10% significance, which can also be expressed as a p value).

In another aspect a plant of the invention or said progeny plants has/have 3, 4, 5, 6, 7, 8, or more or all of the distinguishing characteristics: 1) average mature fruit length; 2) average mature fruit diameter; 3) average mature fruit weight ; 4) average number of flowers in inflorescence; 5) average thickness of pericarp of mature fruit; 6) relative maturity type in area tested; 7) average pedicel (from joint to calyx attachment) length; 8) average number of nodes before first inflorescence; 9) typical size of canopy; and 10) leaf type, in addition to 3, 4, 5, 6, 7, 8, or more, or all of the other (average) characteristics as listed in Table 1 and/or 2. NUN 09168 TOF is a fresh tomato producing small tomato fruits.

Further, a tomato fruit produced on a plant grown from these seeds is provided.

In yet another embodiment of the invention, a plant having one, two or three physiological and/or morphological characteristics which are different from those of NUN 09168 TOF and which otherwise has all the physiological and morphological characteristics of NUN 09168 TOF as listed in Table 1 and/or 2, wherein a representative sample of seed of variety NUN 09168 TOF has been deposited under Accession Number NCIMB 42501, is provided.

Further, a vegetatively propagated plant of variety NUN 09168 TOF, or a part thereof, is provided having all the morphological and physiological characteristics of NUN 09168 TOF when grown under the same environmental conditions.

Also a plant part derived from variety NUN 09168 TOF is provided, wherein said plant part is selected from the group consisting of: fruit, harvested fruit, parts of fruits, leaf, pollen, ovule, cell, part of a leaf, petioles, shoots or parts thereof, stems or parts thereof, roots or parts thereof, cuttings, seeds, parts of seeds, seedcoat, or another maternal tissue which is part of a seed grown on NUN 09168 TOF, hypocotyl, cotyledon, flowers or parts thereof, scion, scion, stock, rootstock and flower. Fruits are particularly important plant parts. In yet another aspect, seeds of NUN 09168 TOF are provided. In still another aspect, seeds growing on plants of NUN 09168 TOF are provided.

DEFINITIONS

"Tomato" refers herein to plants of the species *Solanum lycopersicum*, or a closely related species, and fruits thereof. *Solanum lycopersicum*, is also known as *Lycopersicon lycopersicum* (L.) H. Karst. or *Lycopersicon esculentum* Mill. The most commonly eaten part of a tomato is the fruit or berry. The fruit comprises pericarp, septa, epidermis, columella, locular cavity, vascular bundles and optionally seed. Pericarp, septa, epidermis, columella, locular cavity, vascular bundles, and seedcoat of the seed are maternal tissues, that is they are genetically identical to the plant on which they grow.

"Cultivated tomato" refers to plants of *Solanum lycopersicum*, or a closely related species, i.e. varieties, breeding lines or cultivars of the species *S. lycopersicum* as well as crossbreds thereof, or crossbreds with other *Solanum* species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of Solanum and related species.

The terms "tomato plant designated NUN 09168 TOF", "NUN 09015", "09168 TOF" or "variety designated 09168 TOF" are used interchangeably herein and refer to a tomato plant of variety NUN 09168 TOF, representative seed of which having been deposited under Accession Number NCIMB 42501.

A "seed of NUN 09168 TOF" refers to an F1 hybrid seed represented by the deposit with Accession Number NCIMB 42501. It contains an embryo of NUN 09168 TOF, or a "F1 hybrid embryo". When said seed is planted, it grows into a plant of NUN 09168 TOF.

A "seed grown on NUN 09168 TOF" refers to a seed grown on a mature plant of NUN 09168 TOF or inside a fruit of NUN 09168 TOF. The "seed grown on NUN 09168 TOF" contains tissues and DNA of the maternal parent, NUN 09085 TOF. The "seed grown on NUN 09168 TOF" contains an F2 embryo. When said seed is planted, it grows into a first generation progeny plant of NUN 09168 TOF.

A "fruit of NUN 09168 TOF" refers to an fruit containing maternal tissues of NUN 09168 TOF as deposited under Accession Number NCIMB 42501. In one option, the fruit contains seed grown on NUN 09168 TOF. In another option, the fruit does not contain seed, that is the fruit is parthenocarpic. The skilled person is familiar with methods for inducing parthenocarpy. Those methods comprise chemically or genetically inducing parthenocarpy. Compounds suitable for chemically inducing parthenocarpy comprise auxins, gibberellins and cytokinins. Methods for genetically inducing parthenocarpy comprise the methods described in WO2008143504, WO1998024301, WO1999021411, WO2000074468 and EP142842.

"Tissue culture" refers to a composition comprising isolated cells of the same or a different type or a collection of such cells organized into parts of a plant. Tissue culture of various tissues of tomato and regeneration of plants therefrom is well known and widely published (see, e.g., Bhatia et al. (2004), Plant Cell, Tissue and Organ Culture 78: 1-21. Similarly, the skilled person is well-aware how to prepare a "cell culture".

"UPOV descriptors" are the plant variety descriptors described for tomato in the "Guidelines for the Conduct of Tests for Distinctness, Uniformity and Stability, TG/44/10 (Geneva 2001), as published by UPOV (International Union for the Protection of New Varieties and Plants, available on the world wide web at upov.int) and which can be downloaded from the world wide web at upov.int/en/publications/tg-rom/tg044/tg_44_10.pdf and is herein incorporated by reference in its entirety.

"USDA descriptors" are the plant variety descriptors for tomato (*Solanum lycopersicum* or *Lycopersicon esculentum* Mill.) as published by the US Department of Agriculture, Agricultural Marketing Service, Plant Variety Protection Office, Beltsville, Md. 20705 (available on the world wide web at ams.usda.gov) and which can be downloaded from the world wide web at ams.usda.gov/ under AMSv1.0/getfile?dDocName=STELDEV3003738.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

As used herein, the term "plant" includes the whole plant or any parts or derivatives thereof, preferably having the same genetic makeup as the plant from which it is obtained, such as plant organs (e.g. harvested or non-harvested fruits), plant cells, plant protoplasts, plant cell tissue cultures or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, parts of seeds, seedcoat, clonally propagated plants, roots, stems, root tips, grafts, scions, rootstocks, parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant.

"Harvested plant material" refers herein to plant parts (e.g. fruits detached from the whole plant) which have been collected for further storage and/or further use.

"Harvested seeds" refers to seeds harvested from a line or variety, e.g. produced after self-fertilization or cross-fertilization and collected.

"REFERENCE VARIETY" refers to the variety Conchita from company De Ruiter seeds, which has been planted in a trial together with NUN 09168 TOF. USDA descriptors of NUN 09168 TOF were compared to the USDA descriptors of REFERENCE VARIETY.

"Internode" refers to a portion of a plant stem between nodes.

"Node" refers to the place on a plant stem where a leaf is attached.

"Rootstock" or "stock" refers to the plant selected for its roots, in particular for the resistance of the roots to diseases or stress (e.g. heat, cold, salinity etc.). Normally the quality of the fruit of the plant providing the rootstock is less important.

"Scion" refers to a part of the plant that is attached to the rootstock. This plant is selected for its stems, leaves, flowers, or fruits. The scion contains the desired genes to be duplicated in future production by the stock/scion plant and may produce the desired tomato fruit.

"Stock/scion" plant refers to a tomato plant comprising a rootstock from one plant grafted to a scion from another plant.

"Grafting" refers to attaching tissue from one plant to another plant so that the vascular tissues of the two tissues join together. Grafting may be done using methods known in the art like: 1) Tongue Approach/Approach Graft, 2) Hole insertion/Terminal/Top Insertion Graft, 3) One Cotyledon/Slant/Splice/Tube Graft and 4) Cleft/Side Insertion Graft A plant having "all the physiological and morphological characteristics" of a referred-to-plant means a plant having the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc.

A plant having "essentially all the physiological and morphological characteristics" of a referred-to-plant means a plant having at least 5 (e.g. 6, 7 or all) of the distinguishing physiological and morphological characteristics (distinguishing characteristics as herein defined) when grown under the same environmental conditions of the referred-to-plant (e.g. a plant from which it was derived such as the progenitor plant, the parent, the recurrent parent, the plant used for tissue- or cell culture, etc.) Alternatively, a plant having "essentially all the physiological and morphological characteristics" of a referred-to-plant means a plant having all the characteristics as listed in Table 1 and/or 2 when grown under the same environmental conditions as a referred-to-plant (e.g. a plant from which it was derived such as the progenitor plant, the parent, the recurrent parent, the plant used for tissue- or cell culture, etc.). In another embodiment, a plant having "essentially all the physiological and morphological characteristics" of a referred-to-plant means a plant having all but 1, 2, 3, 4 or 5 of the characteristics as listed in Table 1 and/or 2 when grown under the same environmental conditions as a referred-to-plant (e.g. a plant from which it was derived such as the progenitor plant, the parent, the recurrent parent, the plant used for tissue- or cell culture, etc.).

For NUN 09168 TOF the distinguishing characteristics are 1) average mature fruit length; 2) average mature fruit diameter; 3) average mature fruit weight; 4) average number of flowers in inflorescence; 5) average thickness of pericarp of mature fruit; 6) relative maturity type in area tested; 7) average pedicel (from joint to calyx attachment) length; 8) average number of nodes before first inflorescence; 9) typical size of canopy; and 10) leaf type.

In certain embodiments the plant of the invention has all the physiological and morphological characteristics, except for certain characteristics mentioned, e.g. the characteristic(s) derived from a converted or introduced gene or trait and/or except for the characteristics which differ.

Similarity between different plants is defined as the number of distinguishing characteristics (or the characteristics as listed in Table 1 and/or 2) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

"Distinguishing characteristics" or "distinguishing morphological and/or physiological characteristics" refers herein the characteristics which are distinguishing between NUN 09168 TOF and other tomato varieties, such as REFERENCE VARIETY, when grown under the same environmental conditions, especially the following characteristics: 1) average mature fruit length; 2) average mature fruit diameter; 3) average mature fruit weight; 4) average number of flowers in inflorescence; 5) average thickness of pericarp of mature fruit; 6) relative maturity type in area tested; 7) average pedicel (from joint to calyx attachment) length; 8) average number of nodes before first inflorescence; 9) typical size of canopy; and 10) leaf type. In one aspect, the distinguishing characteristics further include at least one, two, three or more (or all) of the characteristics listed in Table 1 and/or 2. All numerical distinguishing characteristics are statistically significantly different at $p \leq 0.05$.

Thus, a tomato plant "comprising the distinguishing characteristics of "NUN 09168 TOF" refers herein to a tomato plant which does not differ significantly from NUN 09168 TOF in characteristics 1) to 5) above. In a further aspect the tomato plant further does not differ significantly from NUN 09168 TOF in one or more, or all characteristics 6) to 10) as mentioned above. In yet a further aspect the tomato plant further does not differ in at least one, two, three, four, five or six (or all) characteristics selected from the characteristics listed in Table 1 and/ or 2. In still another aspect the tomato plant does not differ in any of the distinguishing characteristics 1) to 10) listed above.

The physiological and/or morphological characteristics mentioned above are commonly evaluated at significance levels of 1%, 5% or 10%, when measured under the same environmental conditions. For example, a progeny plant of NUN 09168 TOF may have one or more (or all) of the essential physiological and/or morphological characteristics of NUN 09168 TOF listed in Table 1 and/or 2, as determined at the 5% significance level when grown under the same environmental conditions.

As used herein, the term "variety", "cultivated tomato" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Plant line" is for example a breeding line which can be used to develop one or more varieties. Progeny obtained by selfing a plant line has the same phenotype as its parents.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Planting" or "planted" refers to seeding (direct sowing) or transplanting seedlings (plantlets) into a field by machine or hand.

"Yield" means the total weight of all tomato fruits harvested per hectare of a particular line or variety. It is understood that "yield" expressed as weight of all tomato fruits harvested per hectare can be obtained by multiplying the number of plants per hectare times the "yield per plant".

"Marketable yield" means the total weight of all marketable tomato fruits, especially fruit that is not cracked, damaged or diseased, harvested per hectare of a particular line or variety.

As used herein, the terms "resistance" and "tolerance" are used interchangeably to describe plants that show no symptoms or significantly reduced symptoms to a specified biotic pest, pathogen, abiotic influence or environmental condition. These terms are also used to describe plants showing some symptoms but that are still able to produce marketable product with an acceptable yield.

"Locus" (plural loci) refers to the specific location, place or site of a DNA sequence on a chromosome, where, for example, a gene or genetic marker is found. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Phenotype" refers to the detectable characteristics of a plant, cell or organism, which characteristics are the manifestation of gene expression.

Haploid" refers to a cell or organism having one set of the two sets of chromosomes in a diploid.

"Diploid" refers to a cell or organism having two sets of chromosomes.

"Polyploid" refers to a cell or organism having three or more complete sets of chromosomes.

"Triploid" refers to a cell or organism having three sets of chromosomes.

"Tetraploid" refers to a cell or organism having four sets of chromosomes.

"Maturity" refers to the fruit developmental stage when the fruit has fully developed (reached its final size), begins to ripen and undergoes ripening, during which fruits can be divided into 1, 2, 3 or more maturity stages. Thereafter, fruits become overripe. In particular embodiments "maturity" is defined as the mature stage of fruit development and optimal time for harvest. In one embodiment a "mature" tomato is defined as having reached the stage of maturity which will insure the proper completion of the normal ripening process. In particular embodiments, fruit should be harvested at a maturity stage i.e. substantially near maximum sweetness and flavor intensity.

"Harvest maturity" is referred to as the stage at which a tomato fruit is ripe or ready for harvest or the optimal time to harvest the fruit. In one embodiment, harvest maturity is the stage which allows proper completion of the normal ripening.

"Flavor" (or flavour) refers to the sensory impression of a food or other substance, especially a tomato fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one tomato line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 09168 TOF. Progeny may be derived by regeneration of cell culture or tissue culture or parts of a plant designated NUN 09168 TOF or selfing of a plant designated NUN 09168 TOF or by producing seeds of a plant designated NUN 09168 TOF. In further embodiments, progeny may also encompass plants derived from crossing of at least one plant designated NUN 09168 TOF with another tomato plant of the same or another variety or (breeding) line, or wild tomato plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to tomato plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a tomato variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a tomato plant by transformation. A plant comprising a transgene stably integrated into its genome is referred to as "transgenic plant".

"Linkage" refers to a phenomenon wherein alleles on the same chromosome tend to segregate together more often than expected by chance if their transmission was independent.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

"Substantially equivalent" refers to a characteristic that, when compared, does not show a statistically significant difference (e.g., p=0.05) from the mean.

The term "mean" refers to the arithmetic mean of several measurements. The skilled person understands that the appearance of a plant depends to some extent on the growing conditions of said plant. Thus, the skilled person will know typical growing conditions for tomatoes described herein. The mean, if not indicated otherwise within this application, refers to the arithmetic mean of measurements on at least 10 different, randomly selected plants of a variety or line.

DETAILED DESCRIPTION

The present invention relates to a *Solanum lycopersicum* variety, referred to as NUN 09168 TOF, which—when compared to REFERENCE VARIETY—has: 1) lower average mature fruit length; 2) lower average mature fruit diameter; 3) lower average mature fruit weight; 4) higher average number of flowers in inflorescence; 5) lower average thickness of pericarp of mature fruit; 6) earlier relative maturity type in area tested; 7) lower average pedicel (from joint to calyx attachment) length; 8) lower average number of nodes before first inflorescence; 9) typical size of canopy that is large; and 10) leaf type that is tomato. Also encompassed by the present invention are progeny plants having all but 1, 2, or 3 of the morphological and/or physiological characteristics of NUN 09168 TOF and methods of producing plants in accordance with the present invention.

A tomato plant of NUN 09168 TOF differs from the most similar comparison variety REFERENCE VARIETY in one or more characteristics (referred herein to as "distinguishing characteristics" or "distinguishing morphological and/or physiological characteristics" (or essential physiological and/or morphological characteristics) selected from: 1) average mature fruit length; 2) average mature fruit diameter; 3) average mature fruit weight; 4) average number of flowers in inflorescence; 5) average thickness of pericarp of mature fruit; 6) relative maturity type in area tested; 7) average pedicel (from joint to calyx attachment) length; 8) average number of nodes before first inflorescence; 9) typical size of canopy; and 10) leaf type.

It is understood that "significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the tomato variety designated NUN 09168 TOF wherein a representative sample of seeds of said variety was deposited under the Budapest Treaty, with Accession number NCIMB 42501.

Seeds of NUN 09168 TOF are obtainable by crossing the male parent with the female parent and harvesting the seeds produced on the female parent. The resultant NUN 09168 TOF seeds can be grown to produce NUN 09168 TOF plants. In one embodiment a plurality of NUN 09168 TOF seeds are packaged into small and/or large containers (e.g., bags, cartons, cans, etc.). The seeds may be disinfected, primed and/or treated with various compounds, such as seed coatings or crop protection compounds.

Also provided are plants of tomato variety NUN 09168 TOF, or a fruit or other plant part thereof, produced from seeds, wherein a representative sample of said seeds has been deposited under the Budapest Treaty, with Accession Number NCIMB 42501. Also included is a cell culture or tissue culture produced from such a plant or a plant regenerated from such a cell or tissue culture said plant expressing all the morphological and physiological characteristics of NUN 09168 TOF optionally as listed in Table 1 and/or 2 when grown under the same conditions.

In one embodiment the invention provides a tomato plant regenerated from the tissue or cell culture of NUN 09168 TOF, wherein the plant has all of the physiological and morphological characteristics of NUN 09168 TOF as listed in Table 1 and/or 2 when determined at the 5% significance level. In another embodiment, the invention provides a tomato plant regenerated from the tissue or cell culture of NUN 09168 TOF, wherein the plant has all of the physiological and morphological characteristics of NUN 09168 TOF when determined at the 5% significance level.

Plants of NUN 09168 TOF can be produced by seeding directly in the ground (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the tomato seed may be planted through a black plastic mulch. The dark plastic will absorb heat from the sun, warming the soil early. It will also help to conserve moisture during the growing season, controls weeds and makes harvesting easier and cleaner. Tomato can also be grown entirely in greenhouses. See for example: M Domis, A P Papadopoulos (2002) Horticultural Reviews for cultivation, harvesting, handling and postharvest methods commonly used.

In another aspect, the invention provides for a tomato plant of variety NUN 09168 TOF, a representative sample of seed from said variety has been deposited under the Budapest Treaty, with Accession number NCIMB 42501.

In other aspects, the invention provides for a fruit of tomato variety NUN 09168 TOF, or a plant part, such as pollen, flowers, shoots or cuttings of variety NUN 09168 TOF or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Tomato (unless indicated otherwise), when grown under the same environmental conditions): 1) average mature fruit length; 2) average mature fruit diameter; 3) average mature fruit weight; 4) average number of flowers in inflorescence; 5) average thickness of pericarp of mature fruit; 6) relative maturity type in area tested; 7) average pedicel (from joint to calyx attachment) length; 8) average number of nodes before first inflorescence; 9) typical size of canopy; and 10) leaf type.

Said tomato variety may further exhibit at least one further trait selected from the group consisting of a) lower average pedicel diameter, b) average internode length after the $2^{nd}$ inflorescence.

In another embodiment the plant of the invention is resistant to some pests and diseases: on a scale of 1 to 9, where 1 is absence of resistance and 9 is highest resistance, NUN 09168 TOF has resistance to *Fusarium oxysporum* f. sp. *Lycopersici* (Fol)—Race 0 (ex 1) and Race 1 (ex 2) that is 9, to *Fusarium oxysporum* f. sp. *radicis lycopersici* (Forl) that is 9, to *Fulvia fulva* (Ff) (ex *Cladosporium fulvum*)— Group A, B, C, D and E that is 9, and to Tomato Mosaic Virus (ToMV) Strain 0, 1 and 2 that is 9.

In still another aspect the invention provides a method of producing a tomato plant, comprising crossing a plant of tomato variety NUN 09168 TOF with a second tomato plant one or more times, and selecting progeny from said crossing. In one embodiment of the invention, the first step in "crossing" comprises planting seeds of a first and a second parent tomato plant, often in proximity so that pollination will occur for example, mediated by insect vectors. Alternatively, pollen can be transferred manually. Where the plant is self-pollinated, pollination may occur without the need for direct human intervention other than plant cultivation.

In yet another aspect the invention provides a method of producing a tomato plant, comprising selfing a plant of tomato variety NUN 09168 TOF one or more times, and selecting progeny from said selfing.

In other aspects, the invention provides for progeny of variety NUN 09168 TOF such as progeny obtained by further breeding NUN 09168 TOF. Further breeding NUN 09168 TOF includes selfing NUN 09168 TOF one or more times and/or cross-pollinating NUN 09168 TOF with another tomato plant or variety one or more times. In particular, the invention provides for progeny that retain all the essential morphological and physiological characteristics of NUN 09168 TOF or that retain one or more of the distinguishing characteristics of the tomato type described further above and when grown under the same environmental conditions. In another aspect, the invention provides for vegetative reproductions of the variety and plants having all but 1, 2, or 3 of the physiological and morphological characteristics of NUN 09168 TOF (e.g. as listed in Table 1 and/ or 2).

The morphological and/or physiological differences between plants according to the invention, i.e. NUN 09168 TOF or progeny thereof, or plants having all but 1, 2, or 3 of the physiological and morphological characteristics of NUN 09168 TOF (as listed in Table 1 and/ or 2; and other known varieties can easily be established by growing NUN 09168 TOF next to the other varieties (in the same field, under the same environmental conditions), preferably in several locations which are suitable for said tomato cultivation, and measuring morphological and/or physiological characteristics of a number of plants (e.g., to calculate an average value and to determine the variation range/uniformity within the variety). For example, trials can be carried out in Acampo, Calif., USA (N 38 degrees 7'261"/W 121 degrees 18'807", USA, whereby, maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of *Solanum*.

The morphological and physiological characteristics (and distinguishing characteristics) of NUN 09168 TOF, are provided in the Examples, in Table 1 and/ or 2. Encompassed herein are also plants derivable from NUN 09168 TOF (e.g. by selfings and/or crossing and/or backcrossing with NUN 09168 TOF and/or progeny thereof) comprising all the physiological and morphological characteristics of NUN 09168 TOF listed in Table 1 and/or 2 as determined at the 5% significance level when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of fruits can be compared, such as cold storage holding quality, post-flesh firmness, and Brix can be measured using known methods.

Flesh firmness can for example be measured using a penetrometer, e.g. by inserting a probe into the fruit flesh and determining the insertion force, or by other methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In a preferred embodiment, the invention provides for tomato fruits of variety NUN 09168 TOF, or a part of the fruit. In another embodiment, the invention provides for a container comprising or consisting of a plurality of harvested tomato fruits or parts of fruits of NUN 09168 TOF, or progeny thereof, or a derived variety.

In yet a further embodiment, the invention provides for a method of producing a new tomato plant. The method comprises crossing a plant of the invention NUN 09168 TOF, or a plant comprising all but 1, 2, or 3 of the morphological and physiological characteristics of NUN 09168 TOF (as listed in Table 1 and/or 2), or a progeny plant thereof, either as male or as female parent, with a second tomato plant (or a wild relative of tomato) one or more times, and/or selfing a tomato plant according to the invention i.e. NUN 09168 TOF, or a progeny plant thereof, one or more times, and selecting progeny from said crossing and/or selfing. The second tomato plant may for example be a line or variety of the species *Solanum Lycopersicon, S. chilense, S. habrochaites, S. penelli, S. peruvianum, S. pimpinellifolium* or other *Solanum* species.

Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another tomato plant (and/or with a wild relative of tomato). Progeny may have all the physiological and morphological characteristics of tomato variety NUN 09168 TOF when grown under the same environmental conditions and/or progeny may have (be selected for having) one or more of the distinguishing characteristics of tomato of the invention. Using common breeding methods such as backcrossing or recurrent selection, one or more specific characteristics may be introduced into NUN 09168 TOF, to provide or a plant comprising all but 1, 2, or 3 or more of the morphological and physiological characteristics of NUN 09168 TOF (as listed in Table 1 and/or 2).

The invention provides for methods of producing plants which retain all the morphological and physiological characteristics of NUN 09168 TOF. The invention provides also for methods of producing a plant comprising all but 1, 2, or 3 or more of the morphological and physiological characteristics of NUN 09168 TOF (e.g. as listed in Table 1 and/or 2), but which are still genetically closely related to NUN 09168 TOF. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 09168 TOF if its DNA fingerprint is at least 80%, 90%, 95% or 98% identical to the fingerprint of NUN 09168 TOF. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Ince et al., (2010) Biochem. Genet. 48:83-95). The invention also provides plants and varieties obtained by these methods. Plants may be produced by crossing and/or selfing, or alternatively, a plant may simply be identified and selected amongst NUN 09168 TOF plants, or progeny thereof, e.g. by identifying a variant within NUN 09168 TOF or progeny thereof (e.g. produced by selfing) which variant differs from NUN 09168 TOF in one, two or three of the morphological and/or physiological characteristics (e.g. in one, two or three distinguishing characteristics), e.g. those listed in Table 1 and/or 2 or others. In one embodiment the invention provides a tomato plant having a Jaccard's Similarity index with NUN 09168 TOF of at least 0.8, e.g. at least 0.85, 0.9, 0.95, 0.98 or even at least 0.99.

The present invention also provides tomato seeds and plants produced by a process that comprises crossing a first parent tomato plant with a second parent tomato plant, wherein at least one of the first or second parent onion plants is a plant provided herein, such as from variety NUN 09168 TOF. In another embodiment of the invention, tomato seed and plants produced by the process are first filial generation (F1) onion seed and plants produced by crossing a plant in accordance with the invention with another, distinct plant.

The present invention further contemplates plant parts of such an F1 tomato plant, and methods of use thereof. Therefore, certain exemplary embodiments of the invention provide an F1 tomato plant and seed thereof.

WO2013182646 which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of NUN 09168 TOF (i.e. is progeny of NUN 09168 TOF), because the seed coat is genetically identical to NUN 09168 TOF. In one embodiment, the present invention relates to a seed coat comprising maternal tissue of NUN 09168 TOF. In another embodiment the invention relates to a tomato seed comprising a seed coat that comprises maternal tissue from NUN 09168 TOF.

By crossing and/or selfing also (one or more) single traits may be introduced into the variety of the invention i.e. NUN 09168 TOF (e.g., using backcrossing breeding schemes), while retaining the remaining morphological and physiological characteristics of NUN 09168 TOF and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 09168 TOF by breeding with NUN 09168 TOF.

Any pest or disease resistance genes may be introduced into a plant according to the invention, i.e. NUN 09168 TOF, progeny thereof or into a plant comprising all but 1, 2, or 3 or more of the morphological and physiological characteristics of NUN 09168 TOF (e.g. as listed in Table 1 and/ or 2). Resistance to one or more of the following diseases is preferably introduced into plants of the invention: Cucumber Mosaic Virus, Curly Top Virus, Tomato Mottle Virus, Potato Y Virus, Blotchey Ripening, Tobacco Etch Virus, the various Tobacco Mosaic Virus races, Concentric cracking, Tomato spotted wilt, Tomato yellows, Gold Fleck, Bacterial canker, Bacterial soft rot, Bacterial speck, Bacterial wilt, Anthracnose (*Gloeosporium piperatum*), *Fusarium* wilt (*F. oxysporum* races), *Alternaria*, Bacterial Spot (*Xanthomonas vesicatoria*), Nematode (*Meloidogyne* spp), Late blight (*Phytophthora infestans* races), Leaf mold (*Cladosporium falvum* races), Colorado potato beetle, Spider mites, Whitefly and *Verticillium* Wilt (*Verticillium dahliae*). Other resistance genes, against pathogenic viruses, fungi, bacteria, nematodes, insects or other pests may also be introduced.

Thus, invention also provides a method for developing a tomato plant in a tomato breeding program, using a tomato plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 09168 TOF or progeny thereof, or a plant comprising all but 1, 2, or 3 or more of the morphological and physiological characteristics of NUN 09168 TOF (e.g. as listed in Table 1 and/or 2), with a different tomato plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Vidaysky and Czosnek, (1998) Phytopathology 88(9): 910-4). For breeding methods in general see Principles of Plant Genetics and Breeding, 2007, George Acquaah, Blackwell Publishing, ISBN-13: 978-1-4051-3646-4.

The invention also provides a tomato plant comprising at least a first set of the chromosomes of tomato variety NUN 09168 TOF, a sample of seed of said variety having been deposited under Accession Number NCIMB 42501; optionally further comprising a single locus conversion, wherein said plant has essentially all of the morphological and physiological characteristics of the plant comprising at least a first set of the chromosomes of tomato NUN 09168 TOF. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 09168 TOF may also be mutated (by e.g. irradiation, chemical mutagenesis, heat treatment, etc.) and mutated seeds or plants or cells may be selected in order to change one or more characteristics of NUN 09168 TOF. Methods such as TILLING may be applied to tomato populations in order to identify mutants. Similarly, NUN 09168 TOF may be transformed and regenerated, whereby one or more chimeric genes are introduced into the variety or into a plant comprising all but 1, 2, 3, or more of the morphological and physiological characteristics (e.g. as listed in Table 1 and/or 2). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 09168 TOF, or progeny thereof, by transforming NUN 09168 TOF or progeny thereof with a transgene that confers the desired trait, wherein the transformed plant retains all the phenotypic and/or morphological and/or physiological characteristics of NUN 09168 TOF or the progeny thereof and contains the desired trait.

The invention also provides a plant or a cell of a tomato plant, a desired trait produced by mutating a tomato plant of variety NUN 09168 TOF or a cell thereof and selecting a plant having the desired trait, wherein the mutated plant retains all or all but one of the phenotypic and morphological characteristics of variety NUN 09168 TOF, optionally as described in Table 1, and contains the desired trait and wherein a representative sample of seed of variety NUN 09168 TOF has been deposited under Accession Number NCIMB 42501.

In a further embodiment, the desired trait is selected from the group consisting of male sterility, herbicide tolerance, insect resistance, pest resistance, disease resistance, environmental stress tolerance, modified carbohydrate metabolism, modified protein metabolism and ripening or the mutation occurs in any of the following genes acs2, acs4, rin, pp2c1, arf9, intense, myb12

The invention also provides for progeny of tomato variety NUN 09168 TOF obtained by further breeding with NUN 09168 TOF. In one aspect progeny are F1 progeny obtained by crossing NUN 09168 TOF with another plant or S1 progeny obtained by selfing NUN 09168 TOF. Also encompassed are F2 progeny obtained by selfing the F1 plants. "Further breeding" encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 09168 TOF when grown under the same environmental conditions. In another embodiment the progeny have one, two, or three distinct traits (qualitative or quantitative) introduced into NUN 09168 TOF, while retaining all the other physiological and morphological characteristics of variety NUN 09168 TOF when grown under the same environmental conditions.

The invention also provides a plant having one, two or three physiological and/or morphological characteristics which are different from those of NUN 09168 TOF and which otherwise has all the physiological and morphological characteristics of NUN 09168 TOF, wherein a representative sample of seed of variety NUN 09168 TOF has been deposited under Accession Number NCIMB 42501. In particular variants which differ from NUN 09168 TOF in none, one, two or three of the characteristics mentioned in Table 1 and/or 2 are encompassed.

In one aspect, the plant having one, two or three physiological and/or morphological characteristics which are different from those of NUN 09168 TOF and which otherwise has all the physiological and morphological characteristics of NUN 09168 TOF differs from NUN 09168 TOF in one, two or three of the distinguishing morphological and/or physiological characteristics selected 1) average mature fruit length; 2) average mature fruit diameter; 3) average mature fruit weight ; 4) average number of flowers in inflorescence; 5) average thickness of pericarp of mature fruit; 6) relative maturity type in area tested; 7) average pedicel (from joint to calyx attachment) length; 8) average number of nodes before first inflorescence; 9) typical size of canopy; and 10) leaf type.

In another embodiment the plant having one, two or three physiological and/or morphological characteristics which are different from those of NUN 09168 TOF and which otherwise has all the physiological and morphological characteristics of NUN 09168 TOF may differ from NUN 09168 TOF in one, two or three morphological or physiological characteristic other than the "distinguishing morphological and/or physiological characteristics" (or essential physiological and/or morphological characteristics) of NUN 09168 TOF selected from: 1) average mature fruit length; 2) average mature fruit diameter; 3) average mature fruit weight; 4) average number of flowers in inflorescence; 5) average thickness of pericarp of mature fruit; 6) relative maturity type in area tested; 7) average pedicel (from joint to calyx attachment) length; 8) average number of nodes before first inflorescence; 9) typical size of canopy; and 10) leaf type.

Tomatoes according to the invention, such as the variety NUN 09168 TOF, or its progeny, or a plant having all physiological and/or morphological characteristics but one, two or three which are different from those of NUN 09168 TOF, can also be reproduced using vegetative reproduction methods. Therefore, the invention provides for a method of producing plants, or a part thereof, of variety NUN 09168 TOF, comprising vegetative propagation of variety NUN 09168 TOF. Vegetative propagation comprises regenerating a whole plant from a plant part of variety NUN 09168 TOF (or from its progeny or from or a plant having all physiological and/or morphological characteristics but one, two or three, which are different from those of NUN 09168 TOF), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets The invention also provides for a vegetatively propagated plant of variety NUN 09168 TOF (or from its progeny or from or a plant having all but one, two or three physiological and/or morphological characteristics which are different from those of NUN 09168 TOF, or a part thereof, having one or more distinguishing characteristics and/or all the morphological and physiological characteristics of NUN 09168 TOF (except for the characteristics differing), when grown under the same environmental conditions.

Parts of NUN 09168 TOF (or of its progeny or of a plant having all physiological and/or morphological characteristics but one, two or three which are different from those of NUN 09168 TOF) encompass any cells, tissues, organs obtainable from the seedlings or plants, such as but not limited to: tomato fruits or parts thereof, cuttings, hypocotyl, cotyledon, seedcoat, pollen and the like. Such parts can be stored and/or processed further. Encompassed are therefore also food or feed products comprising one or more of such parts, such as canned, chopped, cooked, roasted, in a sauce, in a sandwich, pasted, puréed or concentrated, juiced, frozen, dried, pickled, or powdered tomato fruit from NUN 09168 TOF or from progeny thereof, or from a derived variety, such as a plant having all but one, two or three physiological and/or morphological characteristics which are different from those of NUN 09168 TOF.

In one aspect haploid plants and/or double haploid plants of NUN 09168 TOF, or a plant having all but one, two or three physiological and/or morphological characteristics which are different from those of NUN 09168 TOF, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 09168 TOF (or from its progeny or from a plant having all but one, two or three physiological and/or morphological characteristics which are different from those of NUN 09168 TOF, or from a vegetatively propagated plant of NUN 09168 TOF (or from its progeny or from a plant having all but one, two or three physiological and/or morphological character-istics which are different from those of NUN 09168 TOF), being selected from the group consisting of: harvested fruits or parts thereof, pollen, cells, leaves or parts thereof, petioles, cotyledons, hypocotyls, seedcoat, shoots or parts thereof, stems or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a tomato fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

In a preferred embodiment, the present invention and/or embodiments thereof relate to food and/or a food product (or a feed) comprising a part of the tomato plant of the invention NUN 09168 TOF (e.g. a fruit or a seed) wherein the genotype of the plant of the invention is present so that the plant or plant part of the invention can still be identified. Methods to identify the genotype of an tomato plant are known in the art and include nucleotide sequence alignment or using molecular markers.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable tomato fruits are generally sorted by size and quality after harvest. Alternatively the tomato fruits can be sorted by expected shelf life, pH or Brix.

Tomatoes may also be grown for use in grafting or inosculation as rootstocks (stocks) or scions (cions). Typically, different types of tomatoes are grafted to enhance disease resistance, which is usually conferred by the rootstock, while retaining the horticultural qualities usually conferred by the scion. It is not uncommon for grafting to occur between cultivated tomato varieties and related *Solanum* species. Methods of grafting and vegetative propagation are well-known in the art.

So in one aspect the invention relates to a plant comprising a rootstock or scion of NUN 09168 TOF.

Using methods known in the art like "reverse synthesis of breeding lines", it is possible to produce parental lines for a hybrid plant such as NUN 09168 TOF; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi: 10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 09168 TOF) comprising the step of making double haploid cells from haploid cells from the plant of the invention (NUN 09168 TOF) or a seed of that plant; and optionally crossing these parental lines to produce and collect seeds. In another aspect, the invention relates to a combination of parental lines produced by this method. In still another aspect said combination of parental lines can be used to produce a seed or plant of NUN 09168 TOF when these parental lines are crossed. In still another aspect, the invention relates to a combination of parental lines from which a seed or plant having all but one, two or three physiological and/or morphological characteristics which are different from those of NUN 09168 TOF can be produced or in another aspect, wherein a seed or plant having the distinguishing characteristics 1) -5) or 1)-10) of NUN 09168 TOF, as herein defined, can be produced when grown under the same environmental conditions. In still another aspect, the invention relates to a combination of parental lines from which a seed or plant having all the characteristics of NUN 09168 TOF as defined in Table 1 and/ or 2 can be produced when grown under the same conditions.

In another alternative aspect, the invention provides a method of introducing a single locus conversion or single trait conversion or a desired trait into NUN 09085 TOF comprising:
  a. obtain a combination of a male and a female parental line of NUN 09085 TOF,
  b. introduce a single locus conversion in at least one of the parents of step a;
  c. crossing the converted parent with the other parent of step a to obtain seed of NUN 09085 TOF
  A combination of a male and a female parental line of NUN 09085 TOF can be generated by methods described herein, for example through reverse breeding;

Step b) of the above method—introduce a single locus conversion in at least one of the parents of step a—may be done through the following method:
  i. obtaining a cell or tissue culture of cells of the parental line of NUN 09085 TOF;
  ii. genetically transforming or mutating said cells;
  iii. growing the cells into a plant; and
  iv. optionally selecting plants that contain the single locus conversion, the single trait conversion or the desired trait.

Step b) of the above method—introduce a single locus conversion in at least one of the parents of step a—may be done through the following method:

i. crossing the parental line of NUN 09085 TOF with a second tomato plant comprising the single locus conversion, the single trait conversion or the desired trait;
  ii. selecting F1 progeny plants that contain the single locus conversion, the single trait conversion or the desired trait;
  iii. crossing said selected progeny plants of step ii with the parental line of step i, to produce a backcross progeny plant;
  iv. selecting backcross progeny plants comprising the single locus conversion, the single trait conversion or the desired trait and otherwise all or all but one, two or three of the morphological and physiological characteristics of the parental line of step i to produce selected backcross progeny plants; and
  v. optionally repeating steps iii and iv one or more times in succession to produce the selected second, third or fourth or higher backcross progeny plants comprising the single locus conversion, the single trait conversion or the desired trait and otherwise all or all but one, two or three of the morphological and physiological characteristics of the parental line of step i to produce selected backcross progeny plants, when grown in the same environmental conditions.

The invention further relates to plants obtained by this method.

The above method is provided, wherein the single locus conversion concerns a trait, wherein the trait is pest resistance or disease resistance.

In one embodiment the trait is disease resistance and the resistance is conferred to Cucumber Mosaic Virus, Curly Top Virus, Tomato Mottle Virus, Potato Y Virus, Blotchey Ripening, Tobacco Etch Virus, the various Tobacco Mosaic Virus races, Concentric cracking, Tomato spotted wilt, Tomato yellows, Gold Fleck, Bacterial canker, Bacterial soft rot, Bacterial speck, Bacterial wilt, Anthracnose (*Gloeosporium piperatum*), *Fusarium* wilt (*F. oxysporum* races), *Alternaria*, Bacterial Spot (*Xanthomonas vesicatoria*), Nematode (*Meloidogyne incognita*), Late blight (*Phytophthora infestans* races), Leaf mold (*Cladosporium fulvum* races), Colorado potato beetle, Spider mites, Whitefly and *Verticillium* Wilt (*Verticillium dahliae*). In another embodiment, this single locus conversion confers a trait selected from the group consisting of male sterility, herbicide tolerance, insect resistance, pest resistance, disease resistance, environmental stress tolerance, modified carbohydrate metabolism, modified protein metabolism and ripening. In a further embodiment, this single locus conversion occurs in any of the following genes acs2, acs4, rin, pp2c1, arf9, intense, myb12

In another aspect, the current invention also relates to a cultivated tomato plant comprising in its genome a genetic determinant conferring a high tomato fruit acidity level. In another aspect the invention relates to a cultivated tomato plant comprising in its genome a genetic determinant conferring a high tomato fruit acidity level and a genetic determinant conferring a high brix level. In one embodiment the tomato plant is a non-transgenic tomato plant.

In still another embodiment the cultivated tomato plant comprising in its genome said genetic determinant conferring a high tomato fruit acidity level has a fruit acidity level higher than 10 mmol $H_3O^+$ per 100 g of tomato fruit e.g. 10.1, 10.2, 10.3, 10.4, 10.5, 10.6 or even higher e.g. 10.7, 10.8, 10.9, 11.0, 11.1 or higher than 11.1 mmol $H_3O^+$ per 100 g of tomato fruit. Optionally the genetic determinant conferring a high tomato fruit acidity level is as obtainable from/obtained from/derived from/derivable from/as present in plants of NUN 09168, seeds of which having been deposited at the NCIMB under deposit number NCIMB 42501.

In yet another embodiment the cultivated tomato plant comprising in its genome a genetic determinant conferring a high tomato fruit acidity level and a genetic determinant conferring a high brix level has a fruit acidity level higher than 10 mmol $H_3O^+$ per 100 g of tomato fruit and a brix level of 8.0 or higher e.g. 8.1, 8.2, 8.3, 8.4, or higher such as higher than 8.5 or even 8.6 or higher. Optionally the genetic determinant conferring a high tomato fruit acidity level and the genetic determinant conferring the recited brix level are as obtainable from/obtained from/derived from/derivable from/as present in plants of NUN 09168, seeds of which having been deposited at the NCIMB under deposit number NCIMB 42501.

In another embodiment the cultivated tomato plant comprising in its genome a genetic determinant conferring a high tomato fruit acidity level and a genetic determinant conferring a high brix level has a fruit acidity level higher than 10.5 mmol $H_3O^+$ per 100 g of tomato fruit and a brix level of 8.0 or higher e.g. 8.1, 8.2, 8.3, 8.4, or higher such as higher than 8.5 or even 8.6 or higher. Optionally the genetic determinant conferring a high tomato fruit acidity level and the genetic determinant conferring the recited brix level are as obtainable from/obtained from/derived from/derivable from/as present in plants of NUN 09168, seeds of which having been deposited at the NCIMB under deposit number NCIMB 42501.

In yet another embodiment the cultivated tomato plant comprising in its genome a genetic determinant conferring a high tomato fruit acidity level and a genetic determinant conferring a high brix level has a fruit acidity level higher than 10.8 mmol $H_3O^+$ per 100 g of tomato fruit and a brix level of 8.0 or higher e.g. 8.1, 8.2, 8.3, 8.4, or higher such as higher than 8.5 or even 8.6 or higher. Optionally the genetic determinant conferring a high tomato fruit acidity level and the genetic determinant conferring the recited brix level are as obtainable from/obtained from/derived from/derivable from/as present in plants of NUN 09168, seeds of which having been deposited at the NCIMB under deposit number NCIMB 42501.

In yet another embodiment the cultivated tomato plant comprising in its genome a genetic determinant conferring a high tomato fruit acidity level and a genetic determinant conferring a high brix level has a fruit acidity level higher than 11.0 mmol $H_3O^+$ per 100 g of tomato fruit and a brix level of 8.0 or higher e.g. 8.1, 8.2, 8.3, 8.4, or higher such as higher than 8.5 or even 8.6 or higher. Optionally the genetic determinant conferring a high tomato fruit acidity level and the genetic determinant conferring the recited brix level are as obtainable from/obtained from/derived from/derivable from/as present in plants of NUN 09168, seeds of which having been deposited at the NCIMB under deposit number NCIMB 42501.

In yet another embodiment the cultivated tomato plant comprising in its genome a genetic determinant conferring a high tomato fruit acidity level and a genetic determinant conferring a high brix level has a fruit acidity level higher than 10 mmol $H_3O^+$ per 100 g of tomato fruit e.g. 10.1, 10.2, 10.3, 10.4, 10.5, 10.6 or even higher e.g. 10.7, 10.8, 10.9, 11.0, 11.1 or higher than 11.1 mmol $H_3O^+$ per 100 g of tomato fruit; and a brix level of 8.5 or higher e.g. 8.5 or even 8.6 or higher. Optionally the genetic determinant conferring a high tomato fruit acidity level and the genetic determinant conferring the recited brix level are as obtainable from/obtained from/derived from/derivable from/as present in plants of NUN 09168, seeds of which having been deposited at the NCIMB under deposit number NCIMB 42501.

In another aspect the plant of the invention comprising in its genome a genetic determinant conferring a high tomato fruit acidity level and a genetic determinant conferring a high brix level further comprises a genetic determinant conferring an average tomato fruits size of less than 1.0 cm. In on embodiment the average fruit diameter is less than 8 mm. Optionally the genetic determinant conferring a high tomato fruit acidity level and the genetic determinant conferring the recited brix level and the genetic determinant conferring a small average tomato fruit diameter are as obtainable from/obtained from/derived from/derivable from/as present in plants of NUN 09168, seeds of which having been deposited at the NCIMB under deposit number NCIMB 42501.

In one embodiment the cultivated tomato plant comprising in its genome a genetic determinant conferring a high tomato fruit acidity level and a genetic determinant conferring a high brix level has a fruit acidity level higher than 10 mmol $H_3O^+$ per 100 g of tomato fruit e.g. 10.1, 10.2, 10.3, 10.4, 10.5, 10.6 or even higher e.g. 10.7, 10.8, 10.9, 11.0, 11.1 or higher than 11.1 mmol $H_3O^+$ per 100 g of tomato fruit; and a brix level of 8.0 or higher; and further comprises a genetic determinant conferring an average tomato fruits size diameter of less than 1.0 cm. Optionally the genetic determinant conferring a high tomato fruit acidity level and the genetic determinant conferring the recited brix level and the genetic determinant conferring a small average tomato fruit diameter are as obtainable from/obtained from/derived from/derivable from/as present in plants of NUN 09168, seeds of which having been deposited at the NCIMB under deposit number NCIMB 42501.

In still another embodiment the cultivated tomato plant comprising in its genome a genetic determinant conferring a high tomato fruit acidity level and a genetic determinant conferring a high brix level has a fruit acidity level higher than 10 mmol $H_3O^+$ per 100 g of tomato fruit e.g. 10.1, 10.2, 10.3, 10.4, 10.5, 10.6 or even higher e.g. 10.7, 10.8, 10.9, 11.0, 11.1 or higher than 11.1 mmol $H_3O^+$ per 100 g of tomato fruit; and a brix level of 8.0 or higher; and further comprises a genetic determinant conferring an average tomato fruit diameter of less than 0.8 cm. Optionally the genetic determinant conferring a high tomato fruit acidity level and the genetic determinant conferring the recited brix level and the genetic determinant conferring a small average tomato fruit diameter are as obtainable from/obtained from/derived from/derivable from/as present in plants of NUN 09168, seeds of which having been deposited at the NCIMB under deposit number NCIMB 42501.

In still another embodiment the cultivated tomato plant comprising in its genome a genetic determinant conferring a high tomato fruit acidity level and a genetic determinant conferring a high brix level has a fruit acidity level higher than 10 mmol $H_3O^+$ per 100 g of tomato fruit e.g. 10.1, 10.2, 10.3, 10.4, 10.5, 10.6 or even higher e.g. 10.7, 10.8, 10.9, 11.0, 11.1 or higher than 11.1 mmol $H_3O^+$ per 100 g of tomato fruit; and a brix level of 8.5 or higher; and further comprises a genetic determinant conferring an average tomato fruit diameter of less than 0.8 cm. Optionally the genetic determinant conferring a high tomato fruit acidity level and the genetic determinant conferring the recited brix level and the genetic determinant conferring a small average tomato fruit diameter are as obtainable from/obtained from/derived from/derivable from/as present in plants of NUN 09168, seeds of which having been deposited at the NCIMB under deposit number NCIMB 42501.

In still another embodiment the cultivated tomato plant comprising in its genome a genetic determinant conferring a high tomato fruit acidity level and a genetic determinant conferring a high brix level has a fruit acidity level higher than 10 mmol $H_3O^+$ per 100 g of tomato fruit e.g. 10.1, 10.2, 10.3, 10.4, 10.5, 10.6 or even higher e.g. 10.7, 10.8, 10.9, 11.0, 11.1 or higher than 11.1 mmol $H_3O^+$ per 100 g of tomato fruit; and a brix level of 8.5 or higher; and further comprises a genetic determinant conferring an average tomato fruit diameter of less than 1.0 cm. Optionally the genetic determinant conferring a high tomato fruit acidity level and the genetic determinant conferring the recited brix level and the genetic determinant conferring a small average tomato fruit diameter are as obtainable from/obtained from/ derived from/derivable from/as present in plants of NUN 09168, seeds of which having been deposited at the NCIMB under deposit number NCIMB 42501.

In still another embodiment the cultivated tomato plant comprising in its genome a genetic determinant conferring a high tomato fruit acidity level has a fruit acidity level higher than 10 mmol $H_3O^+$ per 100 g of tomato fruit e.g. 10.1, 10.2, 10.3, 10.4, 10.5, 10.6 or even higher e.g. 10.7, 10.8, 10.9, 11.0, 11.1 or higher than 11.1 mmol $H_3O^+$ per 100 g of tomato fruit; and further comprises a genetic determinant conferring an average tomato fruit diameter of less than 0.8 cm. Optionally the genetic determinant conferring a high tomato fruit acidity level and the genetic determinant conferring a small average tomato fruit diameter are as obtainable from/obtained from/derived from/derivable from/as present in plants of NUN 09168, seeds of which having been deposited at the NCIMB under deposit number NCIMB 42501.

In still another embodiment the cultivated tomato plant comprising in its genome a genetic determinant conferring a high tomato fruit acidity level has a fruit acidity level higher than 10 mmol $H_3O^+$ per 100 g of tomato fruit e.g. 10.1, 10.2, 10.3, 10.4, 10.5, 10.6 or even higher e.g. 10.7, 10.8, 10.9, 11.0, 11.1 or higher than 11.1 mmol $H_3O^+$ per 100 g of tomato fruit; further comprises a genetic determinant conferring an average tomato fruit diameter of less than 1.0 cm. Optionally the genetic determinant conferring a high tomato fruit acidity level and the genetic determinant conferring a small average tomato fruit diameter are as obtainable from/ obtained from/derived from/derivable from/as present in plants of NUN 09168, seeds of which having been deposited at the NCIMB under deposit number NCIMB 42501.

It is understood that fruit size can be determined by measuring the tomato fruit diameter. The fruit diameter should be determined by cutting the tomato fruit in 2 halves perpendicular to the longitudinal section. It is understood that when reference is made to fruit diameter, it should be read as maximum fruit diameter.

Longitudinal section is defined according to UPOV publication TG/44/10 for tomato 2001-04-04 at page 24 as can be found on the worldwide web at upov.int under /en/ publications/tg-rom/tg044/tg_44_10.pdf. A longitudinal section of a tomato fruit is thus defined as fruit shape when a tomato fruit is cut in halves from the peduncle end to the blossom end.

The term "genome" relates to the genetic material of an organism. It consists of DNA. The genome includes both the genes and the non-coding sequences of the DNA.

The term "genetic determinant" relates to the genetic information in the genome of the plant that causes a particular trait of a plant.

The term "genetic determinant conferring a high tomato fruit acidity level relates to the genetic information in the genome of the plant that causes the trait tomato fruit acidity level in red ripe fruits of the plants of the invention. The genetic determinant conferring a high tomato fruit acidity level, is the genetic information (gene or locus or introgression) that confers the tomato fruit acidity level. It can be one gene or two or even more genes (or one Quantitative Trait Locus (QTL) or two or more Quantitative Trait Loci (QTLs)).

The term "genetic determinant conferring a high brix level" relates to the genetic information in the genome of the plant that causes the brix level of the fruits of the plants of the invention. The genetic determinant conferring a high brix level is the genetic information (gene or locus or introgression) that confers the brix level of the tomato fruits. It can be one gene or two or even more genes (or one Quantitative Trait Locus (QTL) or two or more Quantitative Trait Loci (QTLs)).

The term "genetic determinant conferring an average tomato fruit diameter relates to the genetic information in the genome of the plant that causes the trait of tomato fruit size diameter in red ripe fruits of the plants of the invention. The genetic determinant conferring an average tomato fruit diameter, is the genetic information (gene or locus or introgression) that confers the tomato fruit diameter. It can be one gene or two or even more genes (or one Quantitative Trait Locus (QTL) or two or more Quantitative Trait Loci (QTLs)).

An allelism test, which is known in the art, can be used to identify if two alleles are located at the same locus.

The word "trait" in the context of this application refers to the phenotype of the plant. When a plant shows the traits of the invention, its genome comprises the genetic determinants causing the traits of the invention. The plant, thus, has the genetic determinants of the invention (high acidity, high brix and small fruit diameter). It is understood that when referring to a plant comprising the trait of the plant of the invention, reference is made to a tomato plant comprising both the trait conferring a high tomato fruit acidity, and the trait conferring a high brix and optionally the trait of small fruit diameter.

A genetic determinant can be inherited in a recessive manner, an intermediate manner, or in a dominant manner Selection for the phenotypic trait is easier when intermediate or dominant inheritance is involved, as a larger part of the progeny of a cross reveals the trait. A genetic determinant can also comprise a combination of recessive and/or intermediate and/or dominant genes or QTLs.

Selection for a genetic determinant can be done on phenotype (the trait that can be observed). Selection can also be done by using one or more molecular markers. The use of molecular markers requires a smaller population for screening (when compared to phenotypical selection), and can be done in a very early stage.

A "plant line" or "breeding line" refers to a plant and its progeny. As used herein, the term "inbred line" refers to a plant line which has been repeatedly selfed and is nearly homozygous for every characteristic. Thus, an "inbred line" or "parent line" refers to a plant which has undergone several generations (e.g. at least 5, 6, 7 or more) of inbreeding, resulting in a plant line with a high uniformity.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (plural loci) means a specific place or places or a site on a chromosome where for example a gene or genetic marker is found. The rust locus (or loci) is thus the location(s) in the genome of a leek plant where the rust resistance-conferring gene is found. Likewise, the purple blotch locus (or loci) is thus the location(s) in the genome of a leek plant where the purple blotch resistance-conferring gene is found.

The term "gene" means a (genomic) DNA sequence comprising a region (transcribed region), which is transcribed into a messenger RNA molecule (mRNA) in a cell, and an operably linked regulatory region (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein. A gene may be an endogenous gene (in the species of origin) or a chimeric gene (e.g. a transgene or cis-gene).

In yet another embodiment the invention relates to a cultivated tomato plant comprising in its genome the genetic determinant conferring a high tomato fruit acidity level and the genetic determinant conferring a high brix level and further comprising the genetic determinant conferring a small average tomato fruit diameter as present in plants of NUN 09168, seeds of which having been deposited at the NCIMB under deposit number NCIMB 42501.

In another embodiment, the plants of the invention have an average fruit weight between 3 and 10 g, preferable between 5 and 7, or even between 5.5 and 6.5 gram.

All documents (e.g., patent publications) are herein incorporated by reference in their entirety.

CITED REFERENCES

Bhatia et al. (2004), Plant Cell, Tissue and Organ Culture 78: 1-21

"Guidelines for the Conduct of Tests for Distinctness, Uniformity and Stability, TG/44/10 (Geneva 2001), as published by UPOV (International Union for the Protection of New Varieties and Plants, available on the world wide web at upov.int) and which can be downloaded from the world wide web at upov.int/en/publications/tg-rom/tg044/tg_44_10.pdf "Objective Description of Variety Tomato (*Lycopersicon esculentum* Mill.)", US Department of Agriculture, Agricultural Marketing Service, Plant Variety Protection Office, Beltsville, Md. 20705 on the worldwide web at ams.usda.gov/sites/default/files/media/55-Tomato%20ST-470-55%202015.pdf M Domis, A P Papadopoulos (2002) Horticultural Reviews for cultivation, harvesting, handling and post-harvest methods commonly used Vos et al. 1995, Nucleic Acid Research 23: 4407-4414

Ince et al., (2010) Biochem. Genet. 48:83-95

Vidaysky and Czosnek, (1998) Phytopathology 88(9): 910-4

Principles of Plant Genetics and Breeding, 2007, George Acquaah, Blackwell Publishing, ISBN-13: 978-1-4051-3646-4

WO2014076249

Nature Protocols Volume: 9, Pages: 761-772 (2014) DOI: doi:10.1038/nprot.2014.049

WO2013182646

EXAMPLES

Development of NUN 09168 TOF

The hybrid NUN 09168 TOF was developed from a male and female proprietary inbred line of Nunhems. The female and male parents were crossed to produce hybrid (F1) seeds of NUN 09168 TOF The seeds of NUN 09168 TOF can be grown to produce hybrid plants and parts thereof (e.g. tomato fruit). The hybrid NUN 09168 TOF can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 09168 TOF is uniform and stable.

Deposit Information

A total of 2500 seeds of the hybrid variety NUN 09168 TOF were deposited according to the Budapest Treaty by Nunhems B.V. on 15 Dec. 2015, at the NCIMB Ltd., Ferguson Building, Craibstone Estate, Bucksburn, Aberdeen AB21 9YA, United Kingdom (NCIMB). The deposit has been assigned NCIMB number 42501. A deposit of NUN 09168 TOF and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808 (b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 09168 TOF is referred to as REFERENCE VARIETY, a variety from De Ruiter Seed with the commercial name Conchita. In Tables 1 and 2 a comparison between NUN 09168 TOF and REFERENCE VARIETY is shown based on a trial in the USA. Trial location Acampo, Calif., USA (38.192873 N 121.232637W). Transplanting date for NUN 09168 TOF: 29 Sep. 2016.

Example 1

Two replications of 50 plants each, from which 15 plants or plant parts were randomly selected, were used to measure characteristics. In Table 1 the USDA descriptors of NUN 09168 TOF (this application) and REFERENCE VARIETY (commercial variety) are listed.

In accordance with one aspect of the present invention, there is provided a plant having the physiological and morphological characteristics of tomato variety NUN 09168 TOF as presented in Table 1.

TABLE 1

Objective description of varieties NUN 09168 TOF and REFERENCE VARIETY

| USDA descriptor | NUN 09168 TOF | REFERENCE VARIETY (Conchita) |
|---|---|---|
| Observation trial planted in: | Acampo, CA, USA | Acampo, CA, USA |
| Observation trial planting type: | Greenhouse | Greenhouse |
| Dates of transplanting | 29 Sep. 2016 | 29 Sep. 2016 |
| Observation trial planting type: | staked | staked |
| Seedling: | | |
| anthocyanin in hypocotyl of 2-15 cm: 1 = absent; 2 = present | 2 | 2 |
| habit of 3-4 week old seedling 1 = normal; 2 = compact | 1 | 1 |
| Mature plant: | | |
| height | NR | NR |
| growth type 1 = indeterminate; 2 = determinate | 1 | 1 |
| form 1 = lax; 2 = normal; 3 = compact; 4 = dwarf; 5 = brachytic | 1 | 1 |
| size of canopy (compared to others of similar form) 1 = small; 2 = medium; 3 = large | 3 | 2 |
| habit 1 = sprawling; 2 = semi-erect; 3 = erect (Dwarf Champion) | 1 | 1 |
| Stem: | | |
| Branching 1 = sparse (Brehm's Solid Red; Fireball); 2 = intermediate (Westover); 3 = profuse (UC 82) | 1 | 1 |
| branching at cotyledon or first leafy node 1 = present; 2 = absent | 2 | 2 |
| number of nodes before first inflorescence 1 = 1-4; 2 = 4-7; 3 = 7-10; 4 = 10 or more | 2 | 3 |
| number of nodes between early ($1^{st}$ to $2^{nd}$, $2^{nd}$ to $3^{rd}$) inflorescence 1 = 1-4; 2 = 4-7; 3 = 7-10; 4 = 10 or more | 2 | 2 |
| pubescence on younger stems 1 = smooth (no long hairs); 2 = sparsely hairy (scattered long hairs); 3 = moderately hairy; 4 = densely hairy or wooly | 3 | 3 |
| Leaf: | | |
| type: 1 = tomato; 2 = potato (Trip-L-Crop) | 1 | 1 |
| Morphology | 3 | 2 |
| margins of major leaflets 1 = absent; 2 = shallowly toothed or scalloped; 3 = deeply toothed or cut, sps. towards base | 2 | 2 |
| marginal rolling or wiltiness 1 = absent; 2 = slight; 3 = moderate; 4 = strong | 1 | 1 |
| onset of leaflet rolling 1 = early-season; 2 = mid-season; 3 = late-season | NA | NA |
| surface of major leaflets 1 = smooth; 2 = rogues (bumpy or veiny) | 1 | 1 |
| pubescence 1 = smooth (no long hairs); 2 = normal; 3 = hirsute; 4 = wooly | 2 | 2 |
| Inflorescence: | | |
| Type 1 = simple; 2 = forked (2 major axes); 3 = compound (much branched) | 1/2 | 1 |
| number of flowers in inflorescence average | 18.7 | 9.5 |
| leafy or "running" inflorescence 1 = absent; 2 = occasional; 3 = frequent | 1 | 1 |
| Flower: | | |
| calyx 1 = normal, lobes awl-shaped; 2 = macrocalyx, lobes large, leaflike; 3 = fleshy | 1 | 1 |
| calyx-lobes 1 = shorter the corolla; 2 = approx., equaling corolla; 3 = distinctly longer than corolla | 1 | 1 |
| corolla color | 1 | 1 |

TABLE 1-continued

Objective description of varieties NUN 09168 TOF and REFERENCE VARIETY

| USDA descriptor | NUN 09168 TOF | REFERENCE VARIETY (Conchita) |
|---|---|---|
| 1 = yellow: 2 = old gold; 3 = white or tan | | |
| style pubescence | 3 | 3 |
| 1 = absent; 2 = sparse; 3 = dense | | |
| anthers | 1 | 1 |
| 1 = all fused into tube; 2 = separating into 2 or more groups at anthesis | | |
| Fasciation (1st flower of 2nd or 3$^{rd}$ inflorescence); | 1 | 1 |
| 1 = absent; 2 = occasionally present; 3 = frequently present | | |
| Fruit: | | |
| typical fruit shape | 3 | 3 |
| shape of transverse section | 1 | 1 |
| 1 = round; 2 = flattened; 3 = angular; 4 = irregular | | |
| shape of stem end | 1 | 1 |
| 1 = flat; 2 = indented | | |
| shape of blossom end | 2 | 2 |
| 1 = indented; 2 = flat; 3 = nippled; 4 = tapered | | |
| shape of pistil scar | 1 | 1 |
| 1 = dot; 2 = stellate; 3 = linear; 4 = irregular | | |
| abscission layer | 1 | 1 |
| 1 = present (pedicellate); 2 = absent (jointless) | | |
| point of detachment of fruit at harvest | 1 | 1 |
| 1 = at pedicel joint; 2 = at calyx attachment | | |
| Length of pedicel (from joint to calyx attachment) mm | 4.9 | 5.71 |
| Length of mature fruit (stem axis) mm | 16.5 | 24.8 |
| Diameter of fruit at widest point mm | 17.4 | 28.4 |
| Weight of mature fruit g | 2.67 | 12.13 |
| Number of locules | 1 | 1 |
| 1 = two; 2 = three or four; 3 = five or more | | |
| Fruit surface | 1 | 1 |
| 1 = smooth; 2 = slightly rough; 3 = moderately rough or ribbed | | |
| Fruit base color (mature-green stage) | 3 | 3 |
| 1 = light green (Lanal; VF 145-F5); 2 = light gray-green; 3 = apple or medium green (Heinz 1439 VF); 4 = yellow green; 5 = dark green | | |
| Fruit pattern (mature-green stage) | 2 | 2 |
| 1 = uniform green; 2 = green-shouldered; 3 = radial stripes on sides of fruit | | |
| shoulder color if different from base | NA | NA |
| 1 = dark green; 2 = grey green; 3 = yellow green | | |
| Fruit color full ripe: | 5 | 5 |
| 1 = white; 2 = yellow; 3 = orange; 4 = pink; 5 = red; 6 = brownish; 7 = greenish; 8 = other | | |
| Flesh color full ripe: | 3 | 3 |
| 1 = yellow; 2 = pink; 3 = red/crimson; 4 = orange; 5 other | | |
| Flesh color: | 1 | 1 |
| 1 = uniform; 2 = with lighter and darker areas in walls | | |
| locular gel color of table-ripe fruit | 3 | 3 |
| 1 = green; 2 = yellow; 3 = red | | |
| ripening | 1 | 1 |
| 1 = blossom to stem end; 2 = uniform | | |
| ripening | 2 | 2 |
| 1 = inside out; 2 = uniformity; 3 = outside in | | |
| stem scar size: | 1 | 1 |
| 1 = small (Roma); 2 = medium (Rutgers); 3 = large | | |
| core: | 1 | 1 |
| 1 = coreless (absent or smaller than 6 × 6 mm); 2 = present | | |
| epidermis color: | 2 | 2 |
| 1 = colorless; 2 = yellow | | |
| epidermis: | 1 | 1 |
| 1 = normal; 2 = easy-peel | | |
| epidermis texture: | 2 | 2 |
| 1 = tender; 2 = average; 3 = tough | | |
| thickness of pericarp: | 2.2 | 4.3 |
| Chemistry and composition of full-ripe fruits: | | |
| pH | NR | NR |
| Titratable acidity as % citric | NR | NR |

TABLE 1-continued

Objective description of varieties NUN 09168 TOF and REFERENCE VARIETY

| USDA descriptor | NUN 09168 TOF | REFERENCE VARIETY (Conchita) |
|---|---|---|
| Total solids | NR | NR |
| Soluble solids as Brix | 6.73 | 6.5 |
| Phenology: | | |
| Seeding to 50% growth (1 open on 50% of plants) | NR | NR |
| Seed to once harvest | NR | NR |
| Fruit season | 2 | NR |
| 1 = long (Marglobe); 2 = medium (Westover); 3 = short, concentrated (VF 145); 4 = very concentrated (UC82) | | |
| Relative maturity in areas tested: | 2 | 4 |
| 1 = early; 2 = medium early; 3 = medium; 4 = medium late; 5 = late; 6 = variable | | |
| Adaptation: | | |
| Culture: | 2 | 2 |
| 1 = field; 2 = greenhouse | | |
| Principle use(s): | 2 | 2 |
| 1 = home garden; 2 = fresh market; 3 = whole-pack canning; 4 = concentrated products 5 = other: Dice | | |
| Machine harvest: | 1 | 1 |
| 1 = not adapted; 2 = adapted | | |
| Regions to which adaptation has been demonstrated: | 9/11 | 9/11 |
| 1 = Northeast; 2 = Mid Atlantic; 3 = Southeast; 4 Florida; 5 = Great Plains, 6 = south central; 7 = Intermountain West; 8 = Northwest; 9 = California (Sacramento and Upper San Joaquin Valley); 10 = California (Coastal Areas); 11 California (Southern San Joaquin Valley & desserts) | | |

TABLE 2

| Non - USDA descriptor | NUN 09168 TOF | REFERENCE VARIETY (Conchita) |
|---|---|---|
| Length of internode after $1^{st}$ inflorescence (cm) | 9.45 | 9.01 |
| Length of internode after $2^{nd}$ inflorescence (cm) | 15.1 | 9.83 |
| Pedicel diameter of mature fruit (mm) | 1.42 | 1.83 |

Table 1 and 2 contain typical values. Values may vary due to environment. Other values that are substantially equivalent are also within the scope of the invention. N.A.=not applicable; n.r.=not recorded.

Example 2

In addition to the USDA descriptors listed in Table 1 and the non USDA descriptors listed in table 2, three characteristics relevant for tomato taste were recorded and compared with 4 other cherry tomato varieties i.e. commercial varieties Juanita and Competition. In addition 2 other Proprietary Nunhems varieties were used. The characteristics of brix, acidity and % juice in tomato in exocarp (i.e. the outermost layer of the pericarp, the wall of the tomato fruit), were recorded according to methods known in the art and outlined below. Plants were grown under standard conditions in a greenhouse in The Netherlands in Spring of 2014. Tomato fruits were harvested early May and the additional characteristics were determined on May 6, 2014. The results of these measurements are listed in Table 3.

Tomato fruit acidity can be determined by collecting fruits of 5 or more e.g. 6, 7, 8, 9,10 or even 11, 12, 13, 14, or 15 or more tomato plants of the same line or variety. Acidity is measured at red ripe stage of the tomato fruits, about 6 days after harvest. It is understood that the first two and the last two tomatoes of each truss are excluded from this measurement Between 20 and 30 fruits of different plants and of different tomato trusses were collected (red ripe, 6 days old). Fruits were macerated using a blender to obtain a homogenized tomato pulp. The amount of titratable acidity in mmol $H_3O^+$ per 100 g fresh weight of pulp was determined using potentiometric titration using a T50 titrator of Mettler Toledo.

Tomato % juice in exocarp.

The % of juice in exocarp was determined by collecting the pericarp of a number of red ripe tomato fruits. Measuring the fresh weight of the collected pericarp tissue. The pericarp tissue was placed between two layers of filtration paper and paper-pericarp-paper sample was compressed to release juice from the pericarp. The released juice was collected in the filtration paper and the amount of juice was measured and expressed as a percentage of the initial pericarp weight.

Brix was recorded using refractometer index

TABLE 3

Brix, Acidity [mmol $H_3O^+$/100 g]and % juice in pericarp of several cherry tomato varieties.

| Variety | Brix | Acidity | % juice in exocarp |
|---|---|---|---|
| Juanita (commercial De Ruiter variety) | 7.6 | 10.4 | 62 |
| Competition (commercial Nunhems BV variety) | 8.3 | 9.7 | 53 |
| Proprietary Nunhems variety 1 | 8.1 | 8.5 | 53 |
| Proprietary Nunhems variety 2 | 8.8 | 9.8 | 62 |
| NUN 09168 TOF | 7.8 | 12.2 | 57 |

Example 3

In 2015, the experiment of 2014 was repeated with 29 other tomato varieties using the same protocols as described in Example 2. This time different tomato types were used.

Plants were grown under standard conditions in a greenhouse in The Netherlands in Summer of 2014. Tomato fruits were harvested early August and the additional characteristics were determined on Aug. 4, 2015. The results of these measurements have been listed in Table 4.

TABLE 4

Type, Brix, Acidity [mmol H3O+/100 g]and % juice in pericarp of several tomato varieties.

| Variety * | Type | Brix | Acidity | % juice in exocarp |
|---|---|---|---|---|
| NUN 09168 TOF | cherry | 8.6 | 11.1 | 58 |
| Competition (commercial Nunhems variety) | cherry | 8.7 | 8.3 | 61 |
| Proprietary Nunhems variety 1 | cherry | 8.0 | 7.2 | 57 |
| Proprietary Nunhems variety 2 | cherry | 8.1 | 8.9 | 58 |
| Proprietary Nunhems variety 3 | cherry | 7.7 | 9.4 | 40 |
| CONCHITA (commercial De Ruiter variety) | cherry | 7.4 | 7.7 | 62 |
| Proprietary Nunhems variety 4 | cherry | 7.6 | 5.9 | 59 |
| Proprietary Nunhems variety 5 | cherry | 7.6 | 7.0 | 54 |
| BRIOSO (commercial Rijk Zwaan variety) | cocktail | 5.9 | 5.7 | 48 |
| Proprietary Nunhems variety 6 | cocktail | 6.6 | 6.1 | 49 |
| Proprietary Nunhems variety 7 | cocktail | 6.0 | 5.6 | 42 |
| Proprietary Nunhems variety 8 | cocktail | 5.1 | 5.4 | 58 |
| Proprietary Nunhems variety 9 | cocktail | 5.8 | 5.5 | 58 |
| AXIRADIUS(commercial Axia variety) | cluster | 4.3 | 4.8 | 31 |
| Proprietary Nunhems variety 10 | cluster | 4.3 | 4.6 | 41 |
| Proprietary Nunhems variety 11 | cluster | 4.3 | 5.0 | 45 |
| Proprietory Nunhems variety 12 | cluster | 4.3 | 4.7 | 37 |
| MERLICE (commercial De Ruiter variety) | cluster | 3.7 | 4.9 | 34 |
| Proprietary Nunhems variety 13 | cluster | 4.1 | 5.0 | 32 |
| Proprietary Nunhems variety 14 | cluster | 4.3 | 6.8 | 22 |
| ARVENTO (commercial Rijk Zwaan variety) | single medium | 4.3 | 4.9 | 30 |
| Proprietory Nunhems variety 15 | single medium | 4.1 | 5.0 | 34 |
| Proprietory Nunhems variety 16 | single medium | 4.4 | 5.3 | 34 |
| Proprietory Nunhems variety 17 | single medium | 4.7 | 5.8 | 44 |
| KANNAVARO (commercial Levarht variety) | single big | 4.4 | 6.4 | 24 |
| Proprietory Nunhems variety 18 | single big | 4.3 | 5.8 | 35 |
| Proprietory Nunhems variety 19 | beef | 4.0 | 4.9 | 29 |
| Proprietory Nunhems variety 20 | single | 4.3 | 4.8 | 23 |
| Proprietory Nunhems variety 21 | single | 5.2 | 5.8 | 22 |
| Proprietory Nunhems variety 22 | single | 5.2 | 5.8 | 26 |

* the proprietary Nunhems varieties were selected from various types of tomatoes such as cherry, cherry cluster, cocktail, cluster medium, cluster big, single medium and single big.

The results of these measurements make clear that NUN 09168 has a % juice in the tomato fruit cell wall that is comparable with other tomato varieties. These measurements further show that tomato fruits of NUN 09168 have a relative high brix level of 8.6 which is comparable with that of variety competition (brix 8.7). The majority of commercial tomatoes have a brix level between 4 and 5, cherry tomatoes normally have a higher brix level of around 8.

Fruits of NUN 09168 TOF also have a relative high acidity of 11.1 mmol $H_3O^+$ per 100 gr which is at least 2.8 mmol higher than the other varieties measured.

Example 4

Traits of the plant of the invention such as fruit acidity level, brix level and fruit size can be transferred to other tomato plants (herein referred as second parent) by crossing NUN 09168 (which has been deposited as NCIMB 42501) with other tomato plants. A breeding program comprising the repetitive execution of the steps of selfing the progeny obtained, selection for the traits of interests (i.e. fruit acidity level, brix level and fruit size) and backcrossing with the second parent (i.e. a breeding method as is known to a person skilled in the art) will result in a tomato plant referred to as second parent additionally comprising the traits of high fruit acidity level, high brix and small fruit size as present in NUN 09168.

What is claimed is:

1. A plant, plant part or seed of tomato variety NUN 09168 TOF, wherein a representative sample of seed of said variety has been deposited under Accession Number NCIMB 42501.

2. The plant part of claim 1, wherein said plant part is a leaf, pollen, an ovule, a fruit, a scion, a rootstock, cutting, flower, or a cell.

3. A seed grown on the plant of claim 1.

4. A tomato plant, or a part thereof which does not differ from the plant of claim 1.

5. A tissue or cell culture of regenerable cells of the plant of claim 1.

6. The tissue or cell culture according to claim 5, comprising cells or protoplasts from a plant part, wherein the plant part is, a meristem, a cotyledon, a hypocotyl, pollen, a leaf, an anther, a root, a root tip, a pistil, a petiole, a flower, a fruit, a stem or a stalk.

7. A tomato plant regenerated from the tissue or cell culture of claim 5, wherein the plant has of the physiological and morphological characteristics of the plant of tomato variety NUN 09168 TOF as listed in Table 1 when grown under the same conditions, wherein a representative sample of seed of said variety has been deposited under Accession Number NCIMB 42501.

8. A method of producing NUN 09168 TOF, or a part thereof, comprising vegetative propagation of the plant of claim 1.

9. The method of claim 8, wherein said vegetative propagation comprises regenerating a whole plant from a part of the plant of NUN 09168 TOF, wherein a representative sample of seed of said variety has been deposited under Accession Number NCIMB 42501.

10. The method of claim 8, wherein said part is a cutting, a cell culture or a tissue culture.

11. A vegetative propagated plant of variety NUN 09168 TOF, or a part thereof having all of the physiological and morphological characteristics of the plant of tomato variety NUN 09168 TOF as listed in Table 1 when grown under the same environmental conditions, wherein a representative sample of seed of tomato variety NUN 09168 TOF has been deposited under Accession Number NCIMB 42501.

12. A method of producing a tomato plant, comprising crossing the plant of claim 1 with a second tomato plant one or more times, and selecting a progeny from said crossing and optionally allowing the progeny to form seed.

13. A tomato plant having all the physiological and morphological characteristics of the plant of claim 1 as listed in Table 1, when grown under the same environmental conditions determined at the 5% significance level, wherein a representative sample of seed of said variety has been deposited under Accession Number NCIMB 42501, further comprising a transgene.

14. A plant of NUN 09168 TOF having all of the morphological and physiological characteristics of the plant of claim 1 when grown under the same environmental conditions, further comprising a single locus conversion, optionally wherein the single locus conversion confers male sterility, herbicide tolerance, insect resistance, pest resistance, disease resistance, environmental stress tolerance, modified carbohydrate metabolism, or modified protein metabolism, wherein a representative sample of seed of NUN 09168 TOF has been deposited under Accession Number NCIMB 42501.

15. A plant comprising the scion or rootstock claim 2.

16. A method of producing double haploids of NUN 09168 TOF comprising making double haploid cells from haploid cells from the plant, plant part or seed of claim 1 by chromosome doubling.

17. A container comprising a plant, plant part or seed of claim 1.

18. A method of producing a modified tomato plant having a single trait, said method comprises mutating a tomato plant or plant part thereof of variety NUN 09168 TOF, wherein a representative sample of said variety has been deposited under Accession Number NCIMB 42501, and wherein the modified plant has all of the physiological and morphological characteristics of variety NUN 09168 TOF and the single trait.

* * * * *